(12) United States Patent
Spediacci et al.

(10) Patent No.: US 7,331,672 B2
(45) Date of Patent: Feb. 19, 2008

(54) STERILE HAND HELD REFRACTIVE SURGERY SLIT LAMP ILLUMINATION SYSTEM

(75) Inventors: Cary Spediacci, Daly City, CA (US); John Weberg, Gilroy, CA (US); Brian Bliven, San Jose, CA (US)

(73) Assignee: VISX, Incorporated, Santa Clara, CA (US)

( * ) Notice: Subject to any disclaimer, the term of this patent is extended or adjusted under 35 U.S.C. 154(b) by 491 days.

(21) Appl. No.: 10/876,268

(22) Filed: Jun. 23, 2004

(65) Prior Publication Data

US 2005/0099602 A1    May 12, 2005

Related U.S. Application Data

(60) Provisional application No. 60/491,909, filed on Aug. 1, 2003.

(51) Int. Cl.
*A61B 3/10* (2006.01)

(52) U.S. Cl. ...................................................... 351/214

(58) Field of Classification Search ......... 351/200–223
See application file for complete search history.

(56) References Cited

U.S. PATENT DOCUMENTS

| | | | | |
|---|---|---|---|---|
| 4,357,079 A * | 11/1982 | Karasawa | ................... | 351/211 |
| 4,801,198 A * | 1/1989 | Heacock et al. | ............ | 351/214 |
| 4,838,679 A | 6/1989 | Bille | ......................... | 351/205 |
| 4,920,467 A | 4/1990 | Honsberger | ................ | 362/226 |
| 5,293,532 A | 3/1994 | Marshall | .................... | 351/225 |
| 5,342,351 A | 8/1994 | Blaha et al. | ................... | 606/4 |
| 5,413,555 A | 5/1995 | McMahan | ....................... | 606/5 |
| 5,437,658 A | 8/1995 | Muller et al. | ............... | 351/205 |
| 5,828,439 A | 10/1998 | Ueno | ......................... | 351/218 |
| 5,861,939 A | 1/1999 | Heacock | ...................... | 607/89 |
| 6,063,108 A | 5/2000 | Salansky | .................... | 351/221 |
| 6,183,086 B1 | 2/2001 | Neubert | ...................... | 607/88 |
| 6,286,958 B1 * | 9/2001 | Koest et al. | ................ | 351/214 |

(Continued)

OTHER PUBLICATIONS

Brochure. SO-801 Hand-held Slit Lamp: Specifications. Scan Optics. 2 pages.

(Continued)

*Primary Examiner*—M. Hasan
(74) *Attorney, Agent, or Firm*—Townsend & Townsend & Crew LLP; Mark D. Barrish

(57) ABSTRACT

A sterile hand held slit lamp for laser refractive surgery includes a charging base that charges a battery while a hand held slit lamp is positioned thereon. A sterile supple cover is positioned over a slit lamp handle while supported by the charging base. A sterile gloved operator grasps the slit lamp handle covered by the sterile cover and illuminates an eye with a slit lamp beam. In many embodiments, an operating microscope provides a view of the eye to an operator while the slit lamp beam illuminates the eye. Operator adjustable controls located on the slit lamp handle are manipulated through a sterile cover and control a length, a width and an intensity of the slit lamp beam. An operator wearing sterile gloves adjusts a position of a piece of tissue near an incision, and removes debris from a surgical incision in tissue after viewing the eye illuminated with the hand held slit lamp beam.

27 Claims, 22 Drawing Sheets

U.S. PATENT DOCUMENTS

| | | | |
|---|---|---|---|
| 6,319,273 B1 | 11/2001 | Chen et al. | 351/221 |
| 6,357,877 B2 | 3/2002 | Takada | 351/221 |
| 6,547,394 B2 | 4/2003 | Doherty | 362/231 |
| 7,083,281 B2 * | 8/2006 | Yogesan et al. | 351/214 |
| 2003/0053310 A1 | 3/2003 | Sommers | 351/212 |
| 2003/0058405 A1 | 3/2003 | Cornsweet et al. | 351/214 |
| 2005/0024587 A1 | 2/2005 | Somani | 351/214 |

OTHER PUBLICATIONS

SO-801 Hand-held Slit Lamp User Manual: Instructions and Specifications. Scan Optics (1999) 14 pages.

* cited by examiner

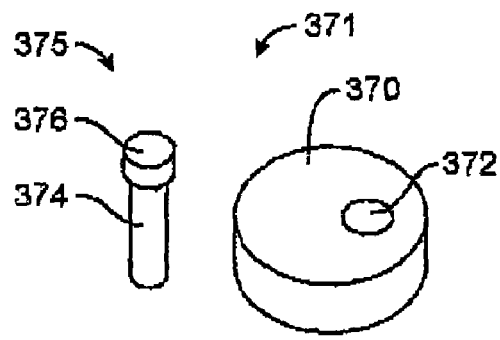
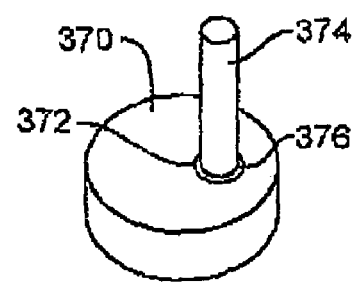
FIG. 6H					FIG. 6I
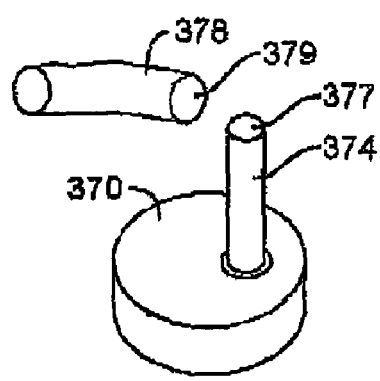
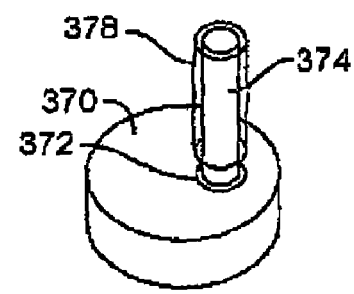
FIG. 6J					FIG. 6K

| Item: 702 | Specification: 700 | Comments: 704 |
|---|---|---|
| HEAD: | | |
| • Lamp Illumination intensity 706 | • Same as SO801 710 | SO801 illumination brightness is good. |
| • Projected Slit width and length. 708<br>Measured 76.2 mm from output of the slit projection illumination head. | Slit width:<br>• (0 – 2 mm) wide continually variable.<br>Slit Length: 712<br>• (1.0 – 8.0 mm) long continually variable | |
| • Slit width control 714 | • Controlled from (0 to 2 mm) maximum via the Physician's thumb, or thumb and forefinger of either hand.<br>• If a ring is used, range from minimum to maximum mechanical motion must be ≤ 1.25 inches.<br>• Clockwise rotation increases from minimum to maximum range adjustment. | |

FIG. 7A

| Item: 702 | Specification: 700 | Comments: 704 |
|---|---|---|
| • Slit length control<br>716 | • Controlled from (1.0 to 8.0 mm) maxiumum via the Physician's thumb, or thumb and forefinger of either hand.<br><br>• If a ring is used, range from minimum to maximum mechanical motion is ≤ 1.25 inches.<br><br>• Clockwise rotation increases from minimum to maxiumu range adjustment. | |
| • Light source<br>718 | White light (Same as ScanOptics® SO801)<br>• Type: Halogen<br>• Rated Life: 22 hrs<br>• Voltage: 3.6 V<br>• Power: 5.83 W<br>• Color Temp: 3300° K | Blue filter is not needed.<br><br>Green filter is not needed. |
| • Light intensity control<br>720 | • Controlled from OFF to Maximum via the Physician's thumb, or thumb and forefinger of either hand.<br><br>• If a ring is used, range from minimum to maximum mechanical motion is ≤ 1.25 inches. | • Detent at "Off", smooth light touch for intensity |

FIG. 7B

| Item: 702 | Specification: 700 | Comments: 704 |
|---|---|---|
|  | • Clockwise rotation increases from minimum to maximum range adjustment. |  |
| • Sterility 722 | - The grip and head controls are able to be, covered with a sterile drape or bag.<br><br>• Sterile bag is designed so that both the (Slit width), (slit length), and (ON/OFF lamp intensity) must be controlled by the physician through the sterile bag.<br><br>• Sterile drape or bag covers head, controls, and battery pack, but not the light projection apparatus. | • One disposable sterile drape or bag used for every treatment procedure. |
| • Eye piece viewer 724 | Not needed for this refractive sugrery operation. | Physician uses the refractive laser system's surgical microscope. |
| • Battery Pack 726 | • Rechargable and located in the head.<br><br>• Continually charged when head is located in charger.<br><br>• No possibility of overcharging.<br><br>• Capacity 45 minutes (1.2 Ah) | • Suggest Litium Ion battery pack, Panasonic (CGR18650) or equivalent<br><br>• Sterile drape or bag should also cover the battery pack since the sterile gloved Physician will be in physical contact.<br><br>• Sterile drape or bag cover head. |

FIG. 7C

| Item: 702 | Specification: 700 | Comments: 704 |
|---|---|---|
| | | controls, and battery pack but not the light projection apparatus. |
| • Slit lamp Batter Contacts: 728 | • Hermetically sealed so that liquid will not enter Slit Head<br>• Gold plated 30 microns (Minimum) | |
| • Slit lamp head switch: 730 | Hermetically sealed so that liquid will not enter Slit Head. | |
| • Weight 732 | ≤ 1.0 lbs. | Includes head and battery pack. |

FIG. 7D

| Item: 735 | Specification: 733 | Comments: |
|---|---|---|
| BATTERY CHARGER STAND ALONE MODEL: —734 | | See Figure 4.0 |
| • AC Power Module  736 | • 115 VAC ± 10% @ 500 ma amps RMS (Max). Line frequency (47-60) Hz. <br><br>• When AC Power is removed a fully charged head will not discharge nor will the spare battery pack. <br><br>• Both battery pack in head and spare battery pack are charged at the same time. <br><br>• Both battery pack in the head and spare battery pack should be fully charged within 2 hours. <br><br>• Charger should have Charging and Fully Charged indicators for both battery pack in the head and spare battery pack. <br><br>• Charging base footprint envelope dimensions. Not to exceed (W x D x H) (4.0 x 7.0 x 5.0 inches) Maximum. <br><br>• Smart charger so as not to overcharge the battery pack | • Does not include the Head and Head battery pack. |
| • Weight 738 | • ≥ 5.0 lbs | • Weighted so that |

FIG. 7E

| Item: 735 | Specification: 733 | Comments: |
|---|---|---|
| | | charger base is sturdy when Physician places or removes the slit lamp from the charger base. |
| • Agency Approvals<br>740 | • ETL Listed<br>• CE certification | |
| STERILITY CHARGER: | | |
| 742 | The charger base is designed so as not to compromise the sterile draped or bagged head and battery pack, when the gloved physician reaches for it. | |

FIG. 7F

| Item: 745 | Specification: 743 | Comments: |
|---|---|---|
| BATTERY CHARGER BUILT-IN MODEL: 744 | | |
| • DC Power Module 746 | • 12 Vdc ± 10% @ 1.0 amp maximum<br><br>• When DC Power is removed a fully charged head will not discharge nor will the spare battery pack.<br><br>• Both battery pack in head and spare battery pack are charged at the same time.<br><br>• Both battery pack in the head and spare battery pack should be fully charged within 2 hours.<br><br>• Charger should have Charging and Fully Charged indicators for both battery pack in the head and spare battery pack.<br><br>• Charging base footprint envelope dimensions. (TBD)<br><br>• Smart charger so as not to overcharge the battery pack. | |

FIG. 7G

| Item: 749 | Specification: 747 | Comments: |
|---|---|---|
| STERILE BAG: 748 | • Disposable. One used for each treatment.<br>• Cost (TBD) | |

FIG. 7H

STERILE HAND HELD REFRACTIVE SURGERY SLIT LAMP ILLUMINATION SYSTEM

CROSS-REFERENCES TO RELATED APPLICATIONS

This is a non-provisional patent application which claims the benefit under 35 USC 119(e) of U.S. Provisional Patent Application No. 60/491,909 filed Aug. 1, 2003, the full disclosure of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

This invention relates generally to medical devices, systems, and methods, and more particularly to slit lamps used to illuminate and view an anterior segment of an eye, optionally during ophthalmic surgery.

Slit lamps are used in ophthalmic applications to view an anterior segment of an eye with a beam of light. The anterior segment of interest typically comprises a cornea, an iris, a sclera, an anterior lens capsule, a posterior lens capsule, and/or a lens nucleus. A beam of light can illuminate these tissues while an operator views an illuminated area through a magnification optic such as a microscope, or by direct examination.

The beam of light from a slit lamp can have a varying beam cross section. For example, in some instances the beam is desirably focused to form a narrow slit. Such a beam is desirable for examining layers of a cornea of an eye. In other instances, for example when viewing a large area of an eye, an operator adjusts the beam to have a wide beam cross section. Slit lamps often pass light through a slot aperture. In many instances, a variation in a size of a light beam is accomplished by mechanically changing a width across a slot aperture.

During LASIK refractive laser surgery a surgeon makes a corneal flap with a microkeratome. The surgeon is typically gloved and sterile during LASIK. After a flap is lifted from a corneal bed, the refractive laser treatment is performed on the stroma, and then the flap is laid back onto the stromal bed. The refractive laser surgeon will often take a patient from a laser system treatment chair to a commercial slit lamp. The surgeon evaluates quality and positioning of the LASIK incision and the resulting flap of tissue with the slit lamp. The beam from a slit lamp can be well suited for viewing debris under a LASIK flap and also for viewing wrinkles in a LASIK flap. Debris and flap wrinkles are appropriately treated and corrected upon detection with a slit lamp examination.

Sterile surgical covers and sterile lamp handles are known. However, these are not ideally suited for use during laser eye surgery and ophthalmic examinations. While ophthalmic slit lamps proposed to date appear to be generally safe for patient examinations during eye surgery, still further improvements would be desirable. In general, slit lamps having improved ease of use without compromising sterility would be desirable. For example, slit lamps permitting sterile evaluation of a patient while a patient remains in a chair of a laser refractive surgery system would be beneficial.

BRIEF SUMMARY OF THE INVENTION

In one aspect, the invention provides a slit lamp for illuminating an eye during ocular surgery. The slit lamp comprises a light slit transmitting window and a handle manually supporting a window. The handle is suitable for supporting the slit lamp with a hand of an operator. A sterile cover covers the handle while held by the operator. In some embodiments, a battery is supported by the handle. At least a portion of the cover is flexible, and the slit lamp includes at least one adjustable control. The adjustable control is covered by the flexible portion of the sterile cover and adjustable by operator manipulations with a hand through the sterile cover. The cover includes an opening disposed between the window and an end of the handle so that the window is exposed while the cover is over the handle. The cover comprises an elongate body extending from an opening to an enclosed end. A first control adjusts a width across the beam of light suitable for projection onto the eye. The first control is adjustable with operator manipulations through the flexible portion of the sterile cover. A second adjustable control adjusts a length across the light beam illuminating the eye. The second control is adjustable with operator manipulations through the flexible portion of the sterile cover.

In specific embodiments, the first control and the second control are adjusted by sliding controls with operator manipulations through the flexible portion of the cover. The first control and the second control can be adjusted by rotating controls with operator manipulations through the flexible portion of the cover. Alternatively, the first control and the second control can be adjusted by applying pressure with operator manipulations through the flexible portion of the cover. The adjustable control can adjust an intensity of the light beam projected onto the eye. Some embodiments comprise a tactile feature configured to be felt by the operator through the cover while the handle is supported by the hand of the operator. The slit lamp can have a plurality of controls. The feature can correspond to a control for adjusting at least one of a length, a width, and an intensity of the light beam such that the operator can identify the corresponding control with the hand. The feature can comprise a tactile orientation feature located on the handle.

Many embodiments comprise a base that charges a battery of the slit lamp, and the cover comprising an opening. A portion of a slit lamp extends through the opening to the base while the battery of the slit lamp is charging, so as to permit an operator to remove the slit lamp from the base by grasping the handle covered with the sterile cover. At least two electrical contacts pass electrical current between the base and the battery. In another embodiment, the base comprises at least one coil of wire charging the battery with an inductive current. The slit lamp is used in conjunction with an operating microscope having a view of the eye while the slit lamp illuminates the eye. In a specific embodiment, the charging base is attached to a laser refractive surgery system. In another, the charging base is placed on a surface of a laser refractive surgery system.

In some embodiments, a slit lamp system comprises a handle having a proximal end and a distal end, and a window is disposed distally of a handle. The window transmits an elongate light beam suitable for illumination of the eye while the handle is supported by a hand of an operator. A battery is supported by the handle and coupled to a charge receiver disposed distally of the handle. A slit lamp receptacle releasably supports the slit lamp distally of the handle. The receptacle has a charge transmitter coupled to a charge receiver so as to charge the battery while the slit lamp is disposed therein. A sterile cover covers the handle. In specific embodiments, the receptacle can be attached to a laser refractive surgery system having an operating microscope, and the receptacle can be adapted to be positioned adjacent to the laser refractive surgery system having the operating microscope. Some embodiments comprise a tactile feature which can be felt by the operator while the handle is supported by the hand of the operator. The feature can correspond to a control for adjusting any one of a length, a width, and an intensity of the light beam. The feature can comprises a tactile orientation feature located on the handle.

In another aspect, the invention comprises a method of viewing an eye during refractive surgery. A portion of a hand held slit lamp is removably covered with a flexible sterile cover. The portion of the hand held slit lamp covered with the sterile cover is grasped by an operator. The eye is illuminated with an elongate beam of light projected from the hand held slit lamp. The illuminated eye is viewed through an operating microscope. Manually manipulating an input of the slit lamp through the sterile cover with a hand adjusts at least one of a width, a length and an intensity of a beam of light. A battery of the hand held slit lamp charges while the slit lamp is placed in a charging base. A portion of the slit lamp is placed in the charging base. In specific embodiments, the charging base can be attached to a laser refractive surgery system, and the charging base can be placed on a surface of the laser refractive surgery system. In some embodiments, an operator can align the light beam with the eye by feeling an orientation of a feature through the cover, and a handle of the slit lamp can be oriented by feeling an orientation of a tactile feature through the cover. An operator can feel a tactile feature corresponding to a control through the cover, and the control can adjust any one of a length, a width and an intensity of the light beam. The operator can adjust the control in response to the feeling.

BRIEF DESCRIPTION OF THE DRAWINGS

FIGS. 6H-6K illustrate a method of using a hand held slit lamp, a charging base and a sterile cover in accordance with a preferred embodiment of the invention.

FIGS. 7A-7D illustrate specifications for a preferred embodiment of a hand held slit lamp in accordance with an embodiment of the invention.

FIGS. 7E and 7F illustrate specifications for a stand alone charging base in accordance with an embodiment of the present invention.

FIG. 7G illustrates specifications for charging base integrated with a laser surgery system in accordance with an embodiment of the present invention.

FIG. 7H illustrates specification for a disposable flexible sterile cover in accordance with an embodiment of the present invention.

DETAILED DESCRIPTION OF THE INVENTION

Figure 1:
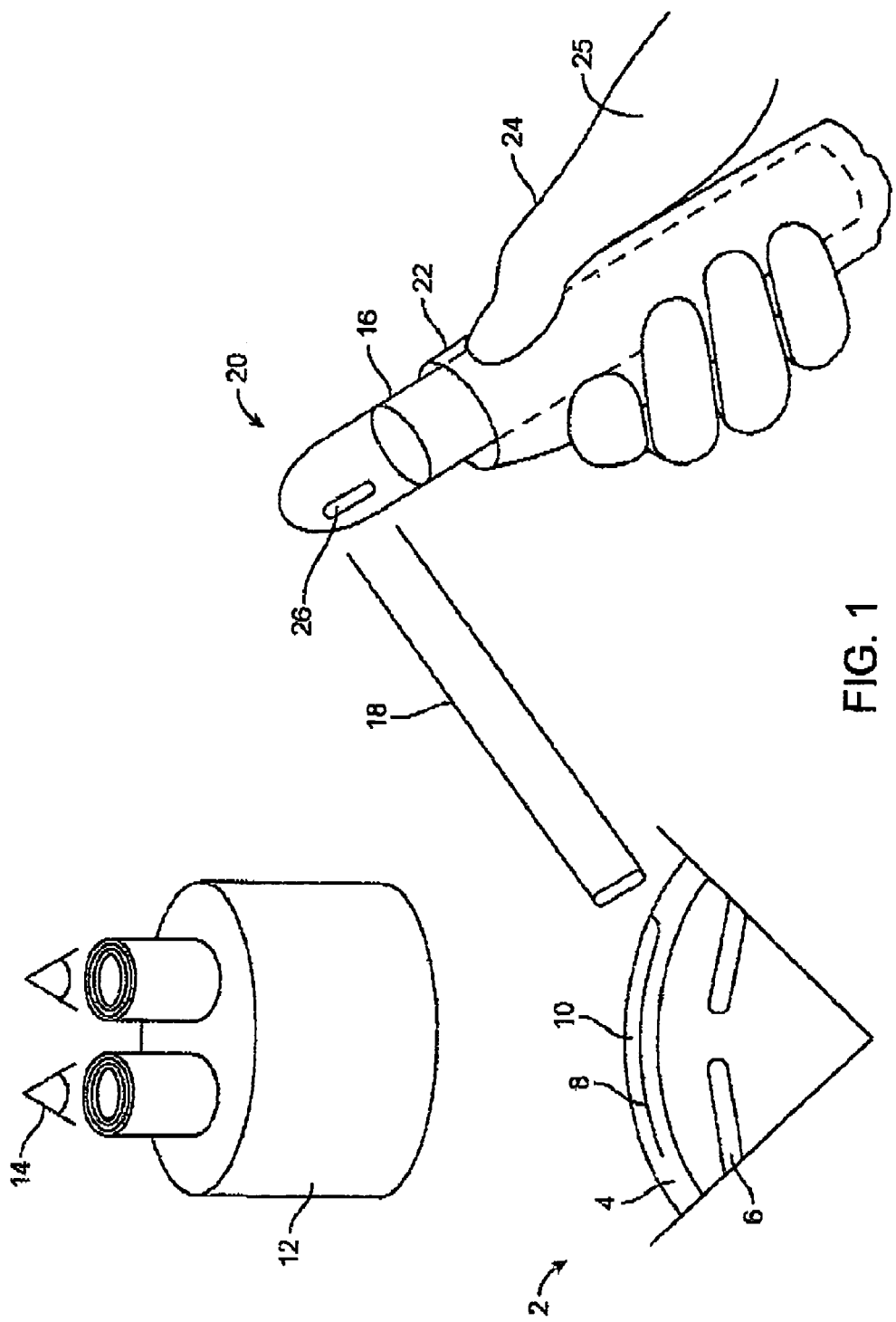
FIG. 1 illustrates a hand held sterile slit lamp illuminating an eye during LASIK eye surgery in accordance with an embodiment of the invention.

As illustrated in FIG. 1, a hand held sterile slit lamp system includes a hand held slit lamp 20 held by a hand 25 of an operator 14 and an operating microscope 12 in accordance with an embodiment of the invention. A sterile glove 24 covers the hand 25 of the operator 14. A sterile flexible disposable cover 22 covers a handle 16 of the hand held slit lamp 20. A beam of light 18 passes through a window 26 of the hand held slit illuminator and illuminates an eye 2. Eye 2 includes a cornea 4, and an iris 6. An incision 8 in cornea 4 is covered by a LASIK flap 10 following cutting with a microkeratome. Operating microscope 12 enlarges a size of eye 2 as seen by operator 14.

Figure 2:
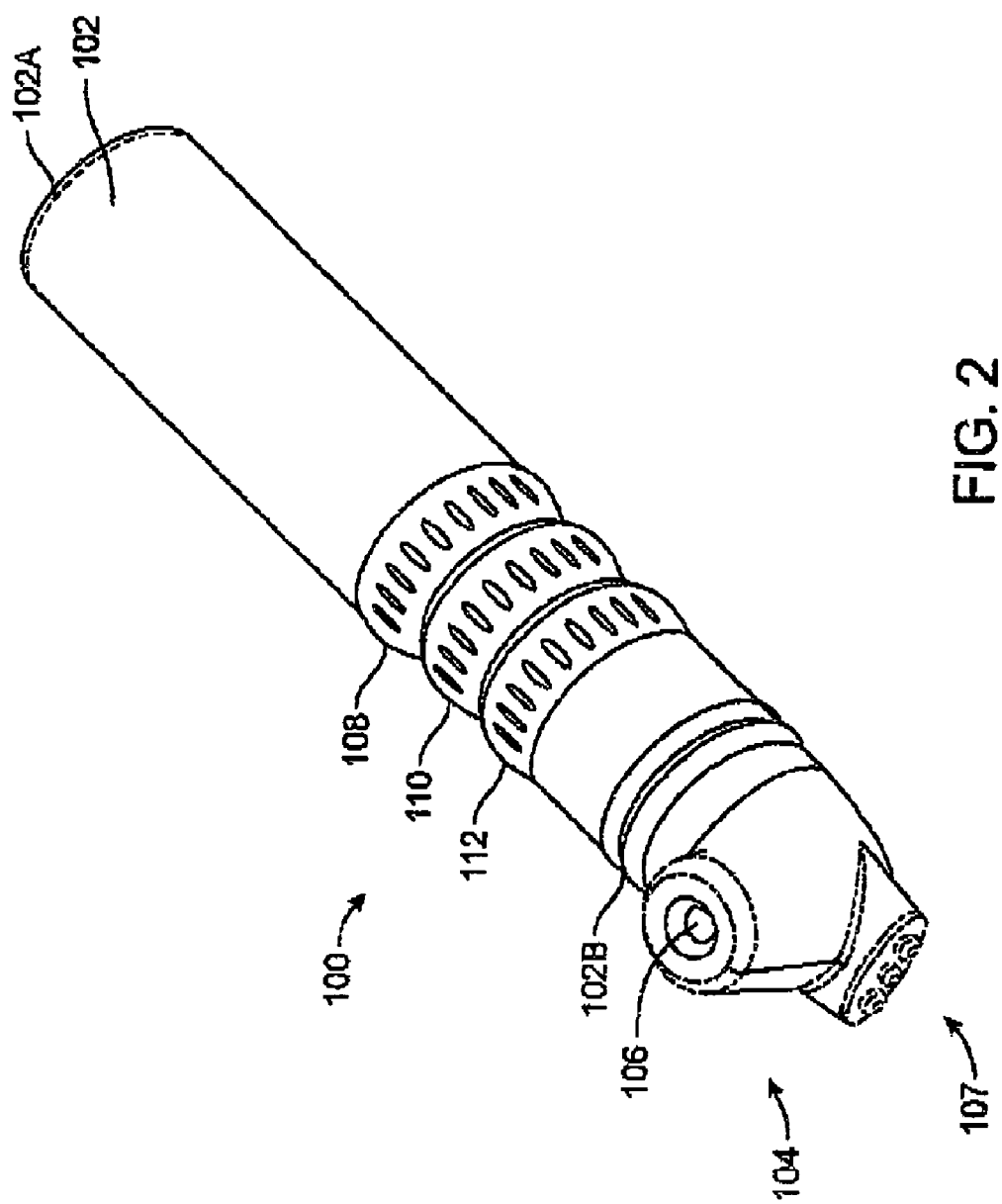
FIG. 2 illustrates a hand held slit lamp in accordance with an embodiment of the invention.

As illustrated in FIG. 2, a hand held slit lamp 100 includes a handle 102 and a head 104 in accordance with an embodiment of the system. Handle 102 includes a proximal end 102A and a distal end 102B. Head 104 includes a window 106 passing a light beam, and electrical contacts 107 passing electrical current. A first control 108 is operator adjustable by rotation and controls an intensity of the projected beam of light. A second control 110 is operator adjustable by rotation and controls a width across a light beam. A third control 112 is operator adjustable by rotation and controls a length across the light beam.

Figure 3:
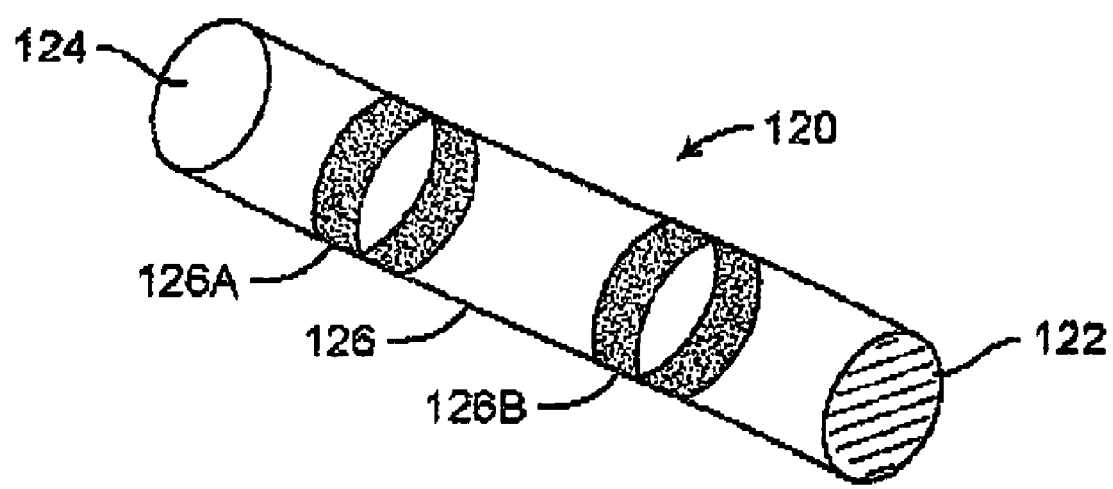
FIG. 3 illustrates a sterile flexible disposable cover to be placed over a handle of a hand held slit lamp in accordance with an embodiment of the invention.

As illustrated in FIG. 3, a sterile disposable cover 120 includes a closed end 122 and an open end 124. The open end 124 receives the handle of sterile slit lamp 100. A flexible portion 126 of cover 120 is located between folds 126A and 126B in cover 120. Flexible portion 126 is positioned over operator adjustable controls 108, 110 and 112 as described above. Sterile cover 120 will typically be primarily or entirely formed of a film material which is flexible and supple, thereby providing the operator with a tactile sensation of holding the handle and a sensation of position of any control as described above. In some embodiments a first portion of cover 120 is flexible and supple and additional portions are stiff as desirable to assist placement of a sterile cover over a handle. In another embodiment a flexible sterile cover has two ends and an opening on each end.

Figure 4:
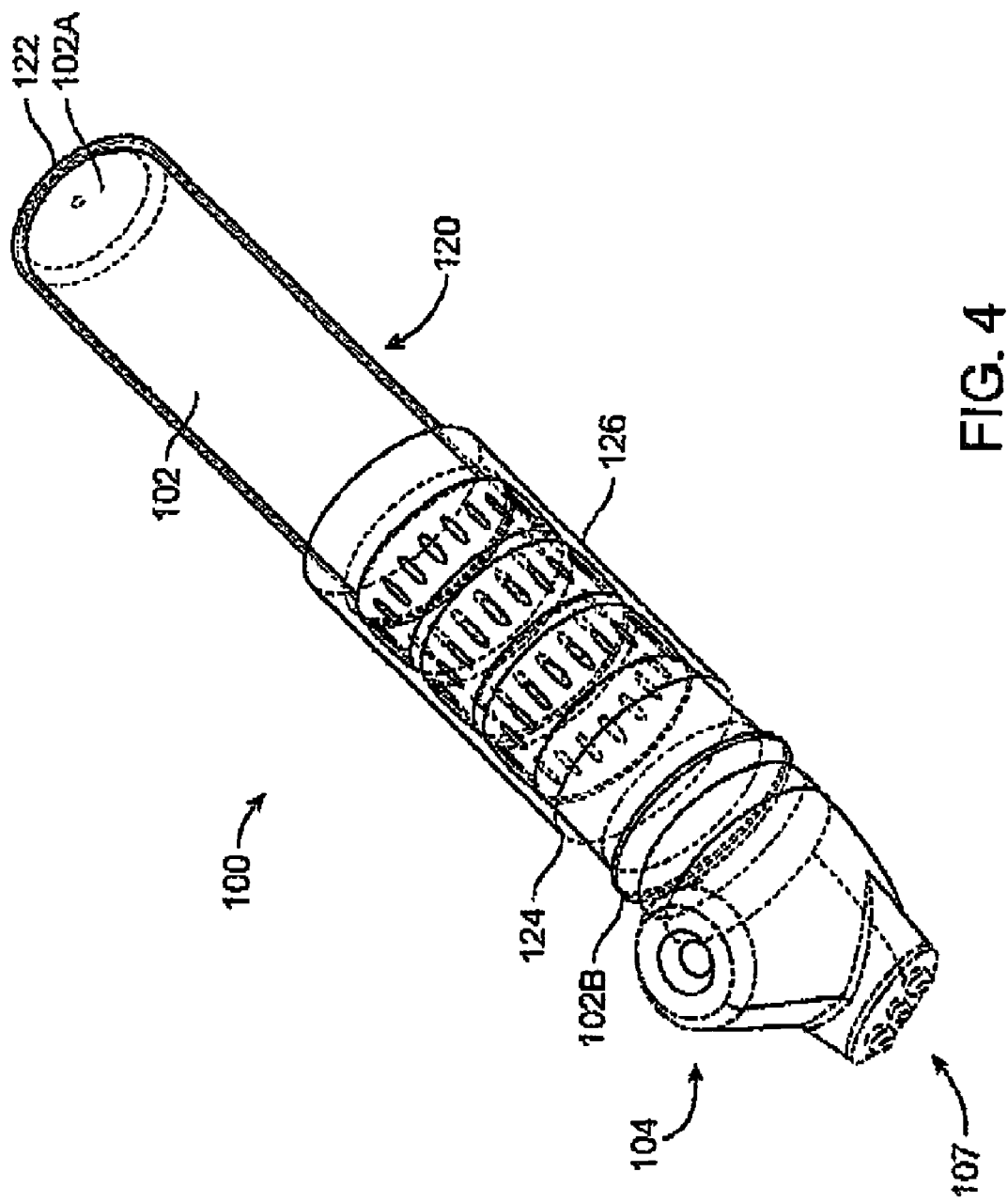
FIG. 4 illustrates a hand held slit illuminator having a handle that is covered with a sterile flexible disposable cover in accordance with an embodiment of the invention.

As illustrated in FIG. 4, an exemplary hand held slit lamp 100 has the handle covered with sterile flexible disposable cover 120. Closed end 122 of cover 120 is positioned adjacent to proximal end 102A of handle 102. The flexible region of cover 126 is positioned over operator adjustable controls 108, 110 and 112 as described above. Distal end 102 B of handle 102 extends through open end 124 in sterile cover 120.

Figure 5:
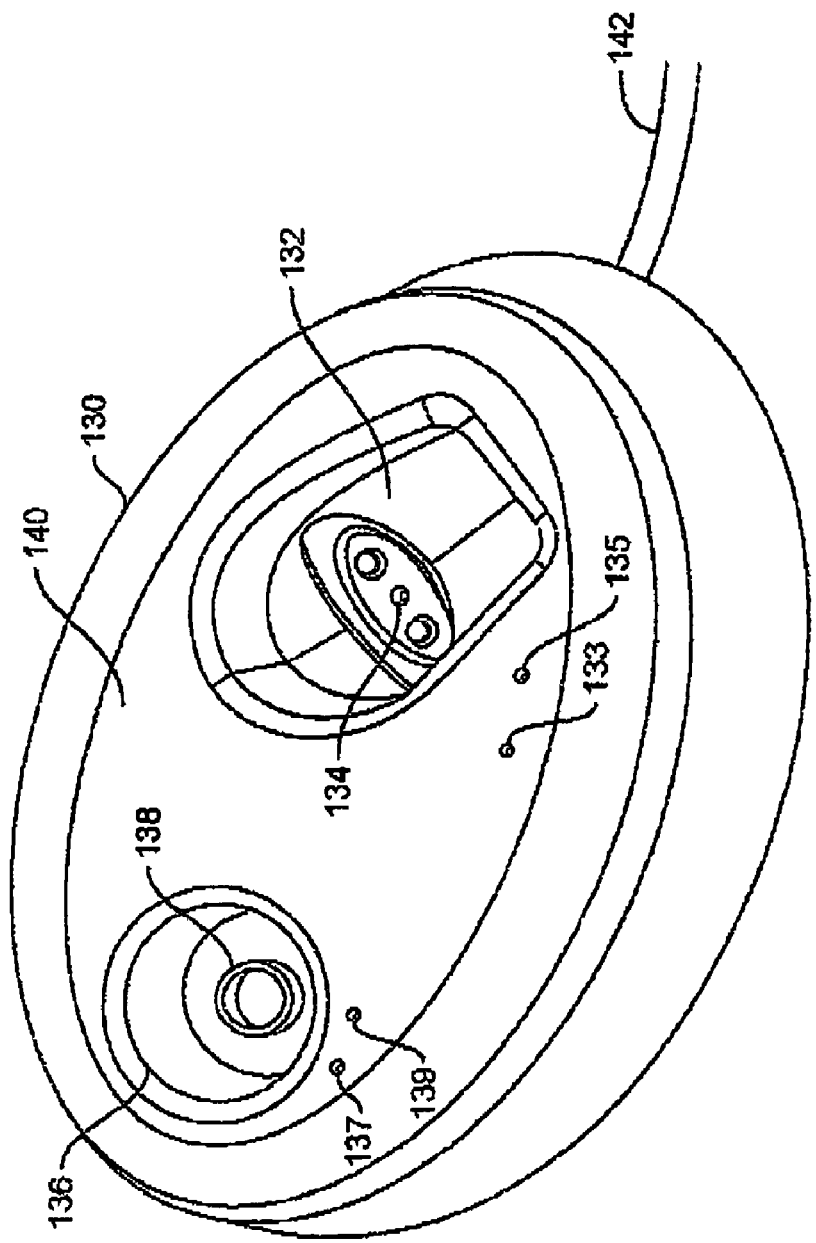
FIG. 5 illustrates a charging base having a receptacle for receiving a head of hand held slit lamp and charging batteries of a slit lamp in accordance with an embodiment of the invention.

As illustrated in FIG. 5, a charging base 130 has a receptacle 132 receiving head 104 of hand held slit lamp 100. A surface 140 is formed to mate base 130 with head 104. Electrical contacts 134 of base 130 are arranged to connect with electrical contacts 107 and pass electrical current when head 104 is positioned in receptacle 132. A second receptacle 136 includes second electrical contacts 138 arranged to connect with electrical contacts of a backup battery. A charging LED 133 of charging base 130 is viewable to the operator and indicates a battery installed in hand held slit lamp 100 is charging by emitting light. A fully charged LED 135 indicates the battery installed in hand held slit lamp 100 is fully charged by emitting light. Another charging LED 137 indicates that the back up battery installed in second receptacle 136 is charging. A fully charged LED 139 again indicates that the back up battery installed in second receptacle 136 is fully charged.

Figure 6:
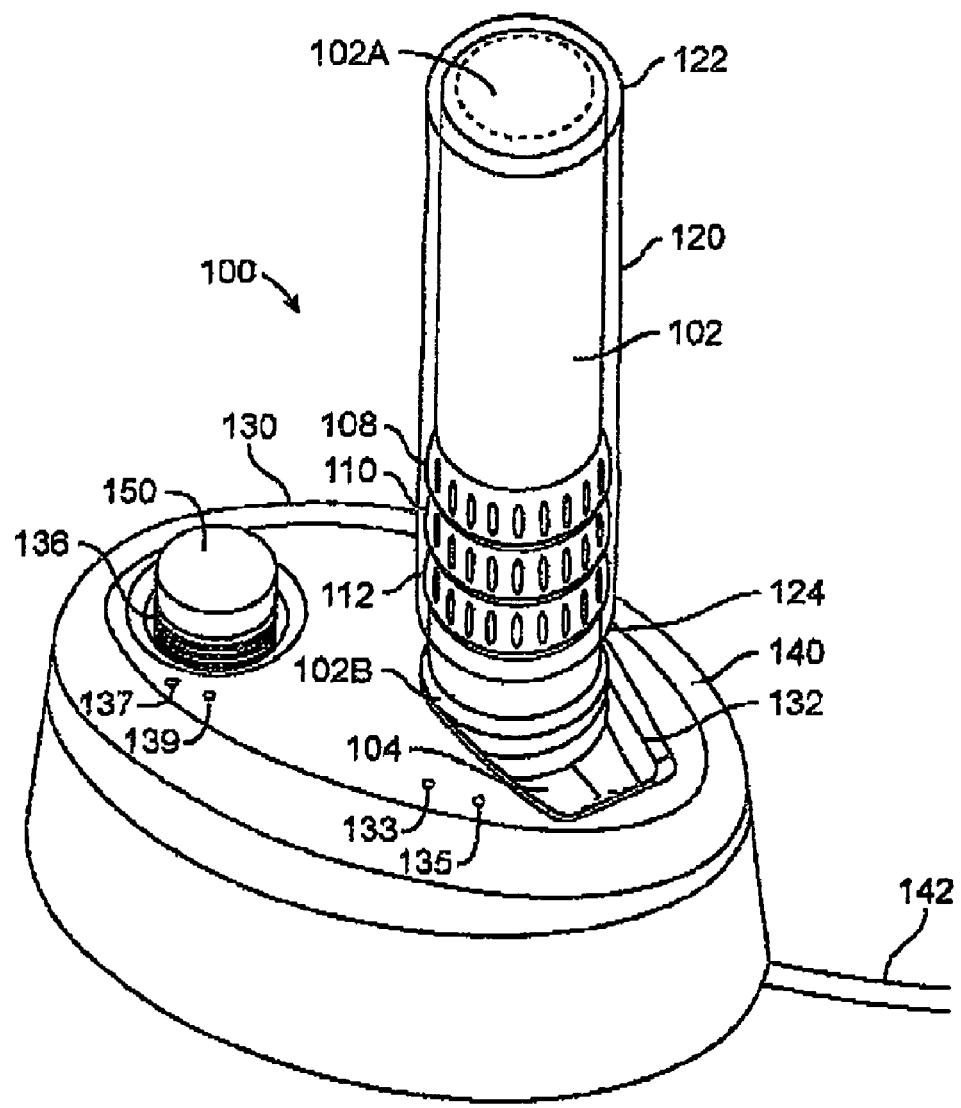
FIG. 6 illustrates a head of a hand held slit lamp inserted into a first receptacle and a battery inserted into a second receptacle of a charging base in accordance with an embodiment of the invention.

As illustrated in FIG. 6, head 104 of hand held slit lamp 100 is inserted into a first receptacle 132 and backup battery 150 is inserted into a second receptacle 136 of charging base 130. Distal end 102B of handle 102 is positioned adjacent to charging base 130, and proximal end 102A of handle 102 is positioned away from base 130. Sterile cover 120 covers most of handle 102, including controls 108, 110 and 112 as described above. Closed end 122 of sterile cover 120 is positioned adjacent to proximal end 102A of handle 102. A portion of handle 102 extends through the opening in open end 124 of sterile cover 120. In an alternate embodiment, sterile cover 120 completely covers handle 102 and a portion of head 104 extends through the opening of open end 124 of sterile cover 120 while the portion of head 104 including window 106 is not covered by sterile cover 120. In another embodiment, the proximal end of handle 102A as described above inserts into the charging base and the cover has two open ends. A first open end of the cover is slid over the handle and placed adjacent to the charging base. A second end of the cover is slid over the window so as not to block light emitted from the window of the slit lamp head.

Figure 6A:
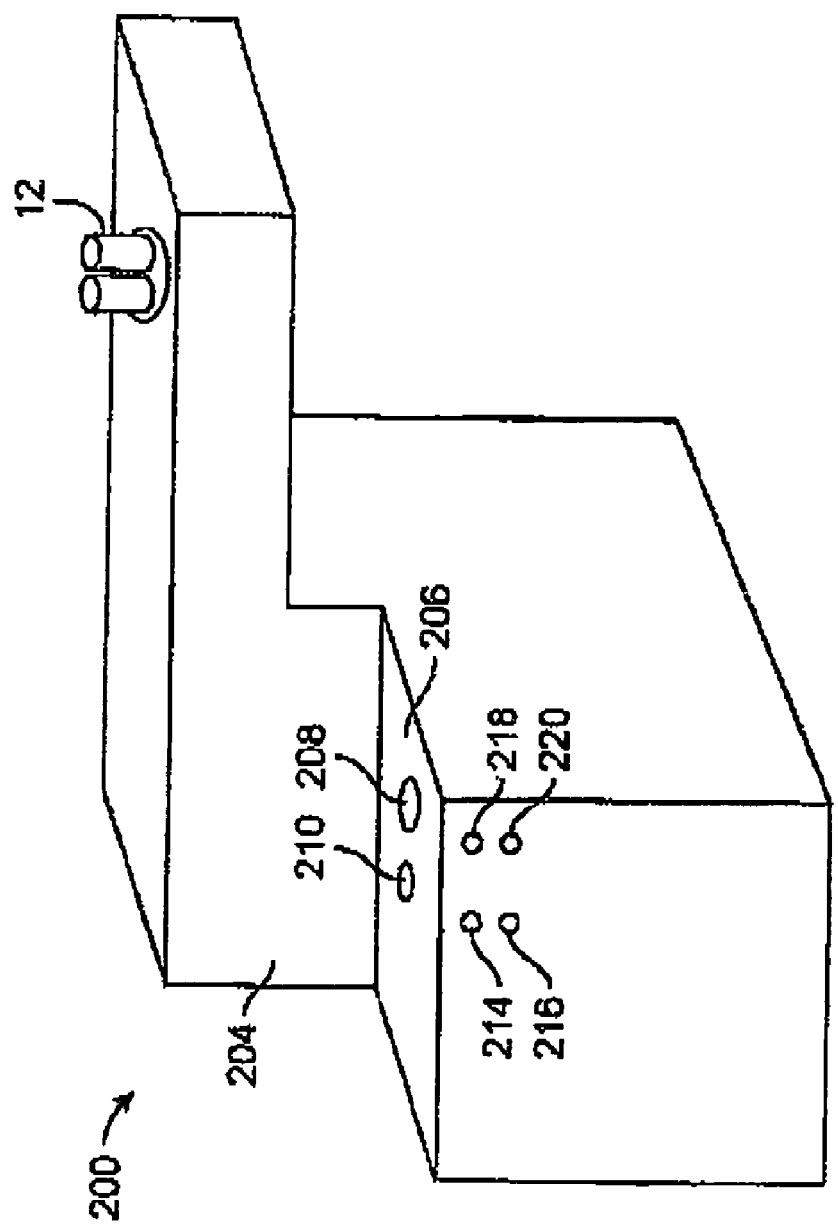
FIG. 6A illustrates a slit lamp receptacle integrated into a refractive laser surgery system in accordance with an embodiment of the invention.

As illustrated in FIG. 6A, a slit lamp receptacle 208 and a battery receptacle 210 as described above are integrated into a refractive laser surgery system 200 in accordance with an embodiment of the invention. A cover 206 is shaped to receive head 104 of hand held slit lamp 100 and battery 150 as described above. Refractive laser surgery system 200 has an LED 218 indicating charging of hand held slit lamp 100 that emits light while the battery of the hand held slit lamp is charging. An LED 220 indicating that the battery of the hand held slit lamp is fully charged emits light while the battery is fully charged and attached to receptacle 208. An LED 214 of back up battery 150 indicates charging of back up battery 150 by emitting light. An LED 216 indicates a fully charged back up battery by emitting light while back up battery 150 is fully charged and attached to receptacle 210. Microscope 12 as described above is integrated into refractive laser surgery workstation 200. Refractive laser surgery workstation 200 preferably comprises a VISX STAR S4™, which is commercially available from VISX, INCORPORATED of Santa Clara, Calif. In alternate embodiments, refractive laser surgery workstation 200 comprises any refractive laser surgery workstation. Examples include the VISX STAR™, STAR S2™, STAR S3® Excimer Laser Systems, which are commercially available from VISX, INCORPORATED of Santa Clara, Calif. Other laser systems include the T-PRKR scanning and tracking laser from Alcon Summit (which acquired the original manufacturer Autonomous Technologies Corporation), the SVS Apex laser from ALCON SUMMIT, the Keracor™ 117 and Technolas® 217A from BAUSCH & LOMB (which acquired the original manufacturers, CHIRON VISION and TECHNOLAS), the LaserSight Laserscan LSX scanning laser from LASERSIGHT, INC., the Meditec MEL-70 and MEL-80 from AESCULAP-MEDITEC, the Esiris available from SCHWIND, the Allegretto Wave from WAVELIGHT TECHNOLOGIES, and the like.

Figure 6B:
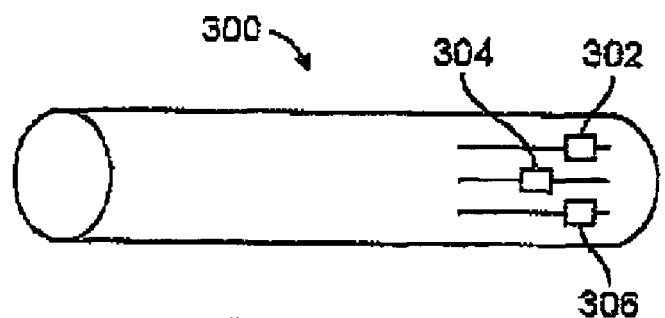
FIG. 6B illustrates a slit lamp having sliding controls located on a handle for adjusting a length, a width, and an intensity of a slit lamp beam in accordance with an embodiment of the invention.

As illustrated in FIG. 6B, a slit lamp handle 300 has sliding controls 302, 304 and 306 adjusting the length, the width, and the intensity, respectively, of the slit lamp beam in accordance with an embodiment of the invention.

Figure 6C:
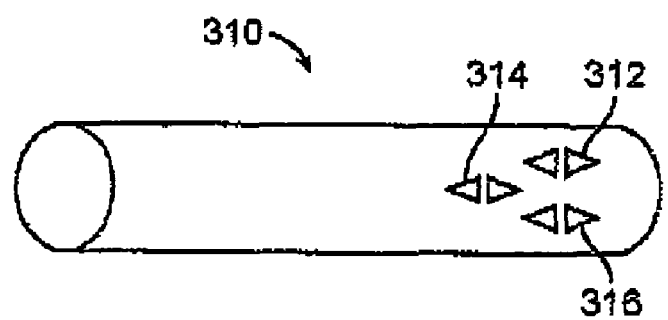
FIG. 6C illustrates a slit lamp having controls responsive to operator hand manipulations with pressure exerted on a control to adjust a length, a width and an intensity of a slit lamp beam in accordance with an embodiment of the invention.

As illustrated in FIG. 6C, a slit lamp handle 310 has controls 312, 314 and 316 responsive to forces from operator hand manipulations to adjust the length, the width and the intensity, respectively, of the slit shaped light beam as described above in accordance with an embodiment of the invention.

Figure 6D:
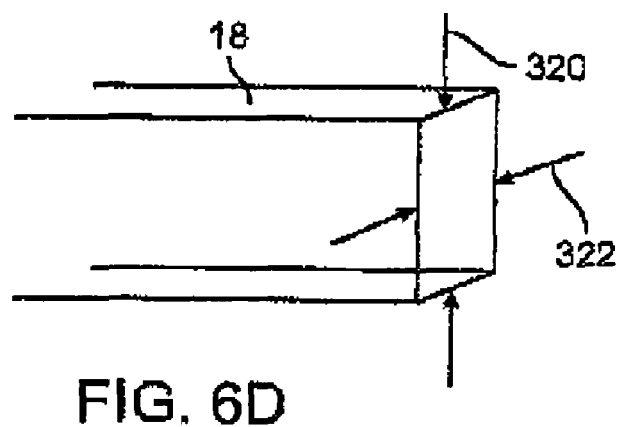
FIG. 6D illustrates a length and a width of a slit lamp beam in accordance with an embodiment of the invention.

FIG. 6D illustrates a length 320 and a width 322 across slit lamp beam 18 in accordance with an embodiment of the invention.

Figure 6E:
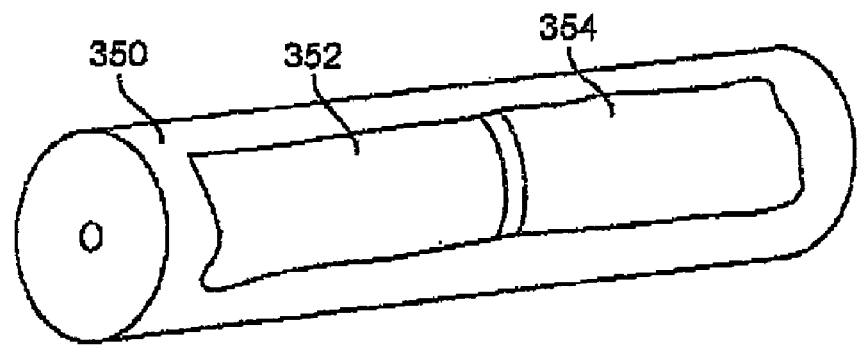
FIG. 6E illustrates a battery pack in accordance with an embodiment of the invention.

FIG. 6E illustrates a battery pack 350 comprising batteries 352 and 354 in accordance with an embodiment of the invention. Batteries 352 and 354 are enclosed within and supported by battery pack 350.

Figure 6F:
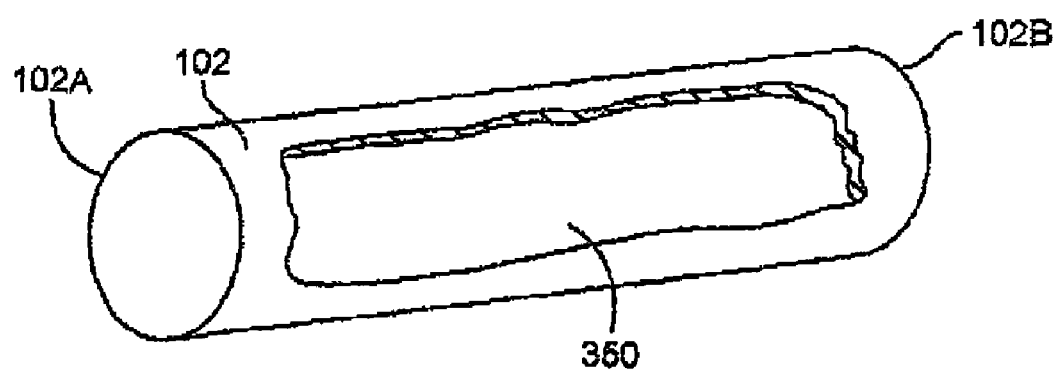
FIG. 6F illustrates a battery pack installed in a handle of a slit lamp in accordance with an embodiment of the invention.

FIG. 6F illustrates battery pack 350 installed in handle 102 of the slit lamp as described above in accordance with an embodiment of the invention. Handle 102 supports battery pack 350 and batteries 352 and 354.

Figure 6G:
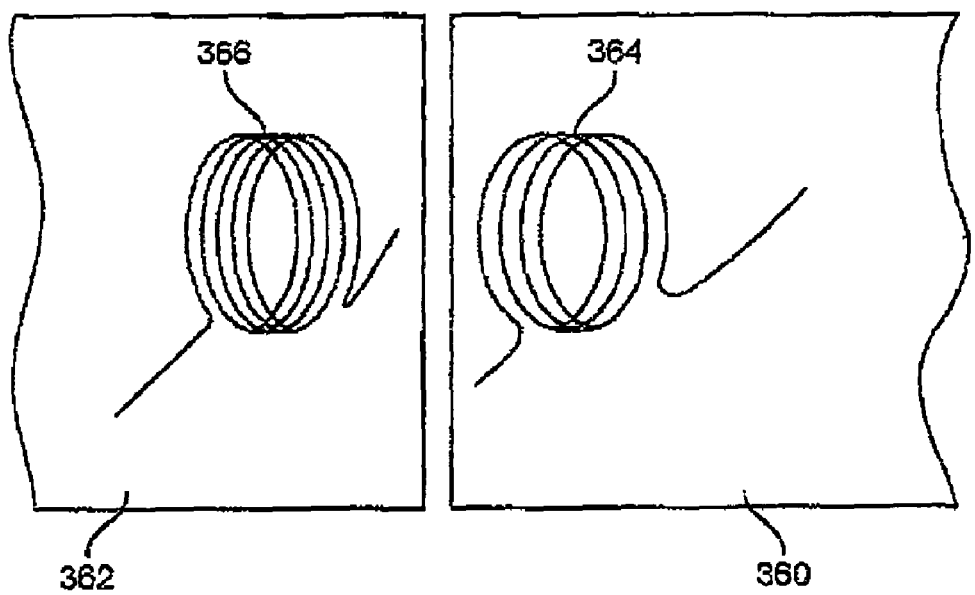
FIG. 6G illustrates a first inductive coil positioned in a charging base inductively coupled to a second inductive coil positioned in a head of a hand held slit lamp in accordance with a preferred embodiment of the invention.

FIG. 6G illustrates a first inductive coil 366 positioned in a charging base 362 and second inductive coil 364 in a handle of a head 360 of a slit lamp in accordance with a preferred embodiment of the invention. First inductive coil 366 is inductively coupled to second inductive coil 364. A varying electrical current in first inductive coil 366 induces a varying inductive current in second coil 364. The inductive current from second inductive coil 364 charges the battery installed in the hand held slit lamp and the back up battery positioned in the charging base as described above.

FIGS. 6H-6K illustrate a method of using a hand held slit lamp system 371 comprising a head 375 with a handle 374, a charging base 370 with a receptacle 372 and a sterile cover 378 in accordance with an embodiment of the invention. Hand held slit lamp system 371 comprises head 375 with handle 374, and base 370 with receptacle 372 as illustrated in FIG. 6H. An operator grasps handle 374 of slit lamp head 375 and inserts a portion 376 of slit lamp head 375 into receptacle 372 of charging base 370. While portion 376 of head 375 is inserted into receptacle 372 as illustrated in FIG. 6I, slit lamp head 375 remains supported by slit lamp charging base 370. As illustrated in FIG. 6J, the operator grasps sterile cover 378 and positions an open end 379 of sterile cover 378 near a proximal end 377 of sterile handle 374. As illustrated in FIG. 6K, sterile cover 378 is positioned over slit lamp handle 374. Sterile cover 378 covers slit lamp handle 374, and the hand of the operator is covered with the sterile glove and grasps the handle covered with the sterile cover as described above.

FIGS. 7A-7D illustrate specifications 700 for several items 702 and comments 704 of a preferred embodiment of a slit lamp in accordance with an embodiment of the invention.

As illustrated in FIG. 7A, the head of the slit lamp includes a lamp intensity 706 which is functionally similar to a commercially available Scan Optics 801 slit lamp, available from Scan Optics of Adelaide, Australia. An operator manual for the SO-801 is available from Scan Optics. The SO-801 hand held slit lamp has slit, rectangular and disc apertures and includes cobalt blue and red free filters. A projected beam slit width and length 708 are measured at a distance of approximately 76.2 mm from an output of head 104 of slit lamp 100 as described above. A width 710 across a slit beam is continuously variable from 0 to 2 mm wide, and a length across a slit lamp beam is continually variable over a range from 1 to 8 mm. A slit width control 714 is controlled from a minimum of 0 mm to a maximum of 2 mm via a physician's thumb, or thumb and fore finger of either hand. For a ring-shaped rotational control, a range of motion when opening a projected slit beam from a minimum to a maximum does not exceed 1.25 inches. A clockwise rotation increases the width of the slit from a minimum value to a maximum value.

As illustrated in FIG. 7B, a slit length control 716 is controlled from a minimum of 1 mm to a maximum of 8 mm with via a physician's thumb, or thumb and fore finger of either hand. For a ring-shaped rotational control, a range of motion when opening the slit from a minimum to a maximum does not exceed 1.25 inches. A clockwise rotation increases a length of a slit from the minimum value to the maximum value. A light source 718 comprises a halogen white light source having a rated life of 22 hours with an applied voltage of 3.6 V and power of 5.83 W providing a color temperature of 3300 degrees Kelvin. A light control intensity 720 is controlled from OFF to a maximum intensity via a physician's thumb, or thumb and forefinger of either hand. For a ring-shaped rotational control, a range of motion when opening a slit from a minimum to a maximum does not exceed 1.25 inches. A clockwise rotation increases an intensity of a projected slit beam from a minimum value to a maximum value.

As illustrated in FIG. 7C, sterility 722 is included as a specification. The handle grip and operator input controls are covered with a sterile drape or bag. The sterile cover comprising a bag is designed so that the projected beam slit width, length and intensity are controlled by a physician operator with hand manipulations through the sterile cover. The sterile cover covers the handle, and operator input controls 108, 110 and 112 controlling the length, the width and the intensity are manipulated through the cover as described above. The sterile cover also covers the first portion of head 104 and does not cover the second portion of head 104 including window 106 as described above. A physician is able to view eye 2 through operating microscope 12 as described above. In an alternate embodiment, an viewer 724 can be attached to the hand held slit lamp. Battery pack 726 includes rechargeable batteries and is located in the handle. Positioning the head in the charging base as described above provides a continual charging of the battery, and batteries are not over charged. A battery pack capacity is 45 minutes. The preferred battery pack is a lithium ion battery pack, such as a Panasonic CGR18650 available from PANASONIC of Elgin, Ill. The sterile drape covers a portion of the head of the slit lamp including the handle comprising the batteries and does not cover the window of the slit lamp as described above.

As illustrated in FIG. 7D, slit lamp battery contacts 728 are hermetically sealed so that a liquid will not enter the head of a slit lamp, and battery contacts comprise plated gold having a minimum thickness of 30 microns. A slit lamp head switch 730 is hermetically sealed so that a liquid will not enter the slit lamp head. Slit lamp head switch 730 automatically turns off the slit lamp while positioned in the charging base. Upon removal from the charging base, the slit lamp head switch automatically turns on the slit lamp. A weight 732 of the head including the battery pack is preferably less than one pound.

FIGS. 7E and 7F illustrate a specification 733 for an item 735 comprising a stand alone battery charging base 734 as described above in accordance with an embodiment of the invention. Stand alone battery charging base 734 includes an AC Power Module 736, rated for 115 Volts, and removal of AC power does not result in a discharge of a charged battery installed in the slit lamp or a charged spare battery. Charging of the battery installed in the slit lamp and the spare battery occur simultaneously. The battery installed in the slit lamp and the spare battery are fully charged in two hours. The base includes a charging and a fully charged light for a battery installed in the slit lamp, and also includes a charging and a fully charged light for a spare battery. The charging base foot print envelope has dimensions that do not exceed a width of 4 inches, a length of 7 inches and a height of 5 inches. A smart charger is included within the charging base to prevent over charging of the battery. A weight 738 of the charging base does not exceed 5 pounds. FIG. 7F illustrates specifications for the stand alone charging base, a specification for the charging base integrated with the laser surgery system, and the disposable flexible sterile cover in accordance with embodiments of the present invention. The charging base is approved by regulatory agencies 740 to provide an ETL listing and a CE Mark certification. As an acronym, ETL stands for Electro-Technical Laboratory, and ETL SEMKO is a worldwide electrical safety testing and certification agency having offices located in San Francisco, Calif. ETL SEMKO is a division of INTERNEK TESTING SERVICES. ETL can certify medical products for compliance in global markets. The term CE Mark stands for CONFORMITÉ EUROPÉAN and a product having such a mark conforms to safety and quality standards set forth by the European Community. The CE Mark is the official marking required by the European Community for all electrical and electronic equipment that is sold or put into service for a first time anywhere in the European Community. An application of a CE Mark to a product requires a compliance statement from a manufacturer or representative in the European Community. Sterility of a charger 742 is enhanced with a charging base having a design so as not to compromise sterility of the head covered by the sterile cover as described above while a physician wearing sterile gloves reaches for and grasps the covered handle of the head of the slit lamp.

As illustrated in FIG. 7G, a specification 743 for an item 745 comprising a built in battery charger 744 is integrated with the laser surgery system as described above in accordance with a preferred embodiment of the invention. A DC power module 746 is powered by 12 volts DC having a maximum current of one amp. A removal of DC power does not result in a discharge of the charged battery installed in the slit lamp or the charged spare battery. Charging of the battery installed in the slit lamp and the spare battery occurs simultaneously. The battery installed in the slit lamp and the spare battery are fully charged in two hours. A built in charger module includes a charging and a fully charged light for the battery installed in the slit lamp, and also includes a charging and a fully charged light for the spare battery. A smart charger is included with a built in charger module to prevent over charging of a battery.

FIG. 7H illustrates a specification 747 for an item 749 which is the flexible sterile cover comprising a sterile bag 748 in accordance with a preferred embodiment of the invention. Sterile bag 748 is disposable and a single bag is used for each treatment. A cost of sterile bag 748 can be determined by requesting a quotation from a vendor. For example, sterile bags are available from Scan Optics as a custom order.

Figure 8A:
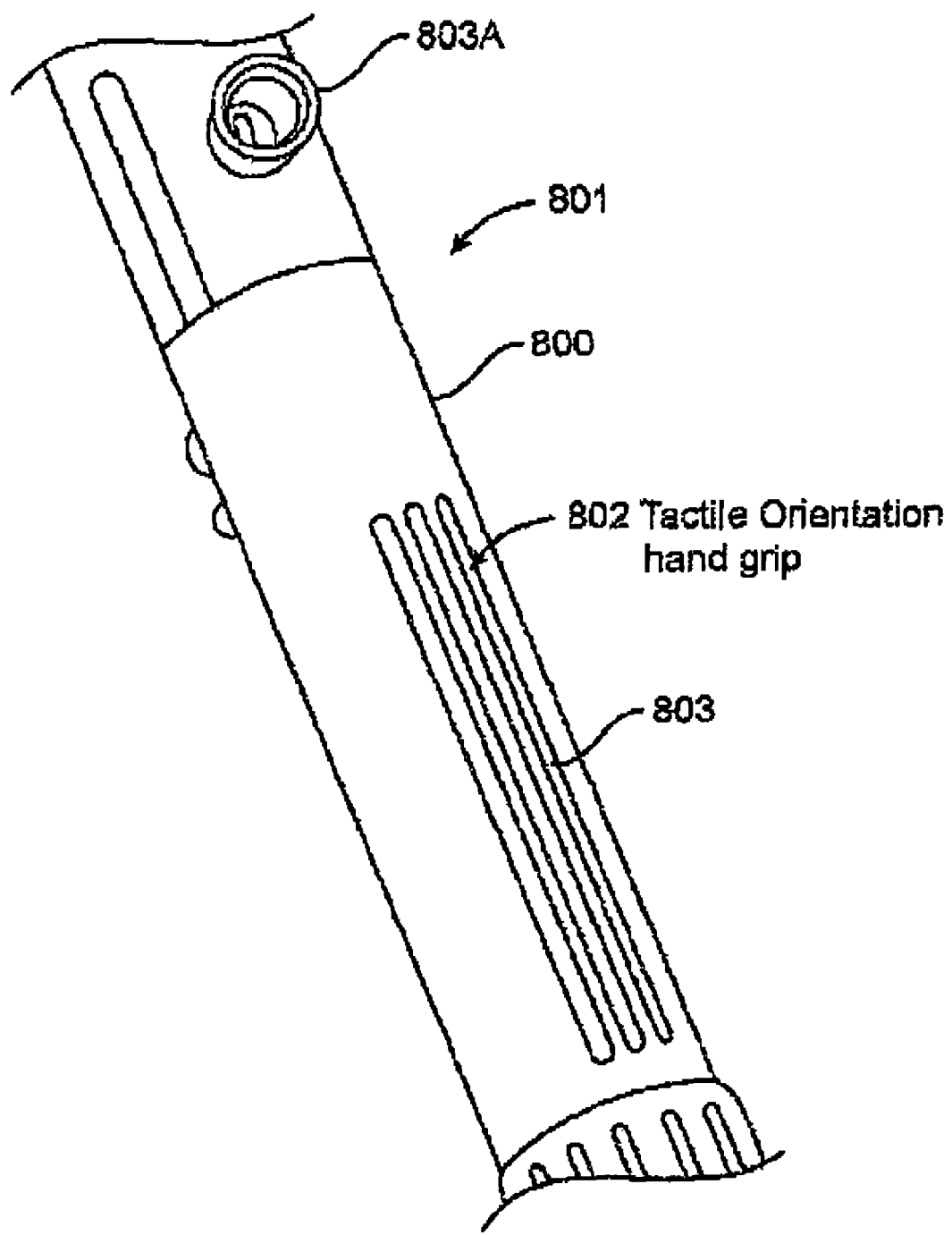
FIG. 8A illustrates a handle having tactile orientation in accordance with an embodiment of the present invention.

As illustrated in FIG. 8A, a slit lamp 801 comprises a handle 800 having a hand grip 802 providing tactile orientation of slit lamp 801 in accordance with an embodiment of the present invention. Tactile orientation facilitates use by an operator wearing sterile gloves while a sterile cover covers the handle and the operator views the eye as described above. Slit lamp 801 comprises a tactile feature which is felt by the operator while the handle is supported by the hand of the operator. Hand grip 802 has a tactile feature such as grooves 803 which provides tactile orientation of the handle with respect to a hand of a operator. The tactile feature such as grooves 803 is aligned with a light transmitting window 803A as described above, and is aligned with the projected beam of light as described above so as to permit the operator to align the projected beam with the eye using tactile sensations from the tactile feature such as grip 802. The operator is able to align the light beam by feeling an orientation of the tactile feature such as grooves 803 through the sterile gloves and the sterile handle cover while the handle is supported by the hand of the operator. The operator orients the handle in response to the orientation and feeling so as to align the light beam with the eye. Slit lamp 801 preferably includes an arrow (not shown) at the top of the slit lamp indicating a direction of the projected light beam, and alignment marks (not shown) on a battery pack and handle for aligning the battery pack to the handle during installation of the battery pack.

Figure 8B:
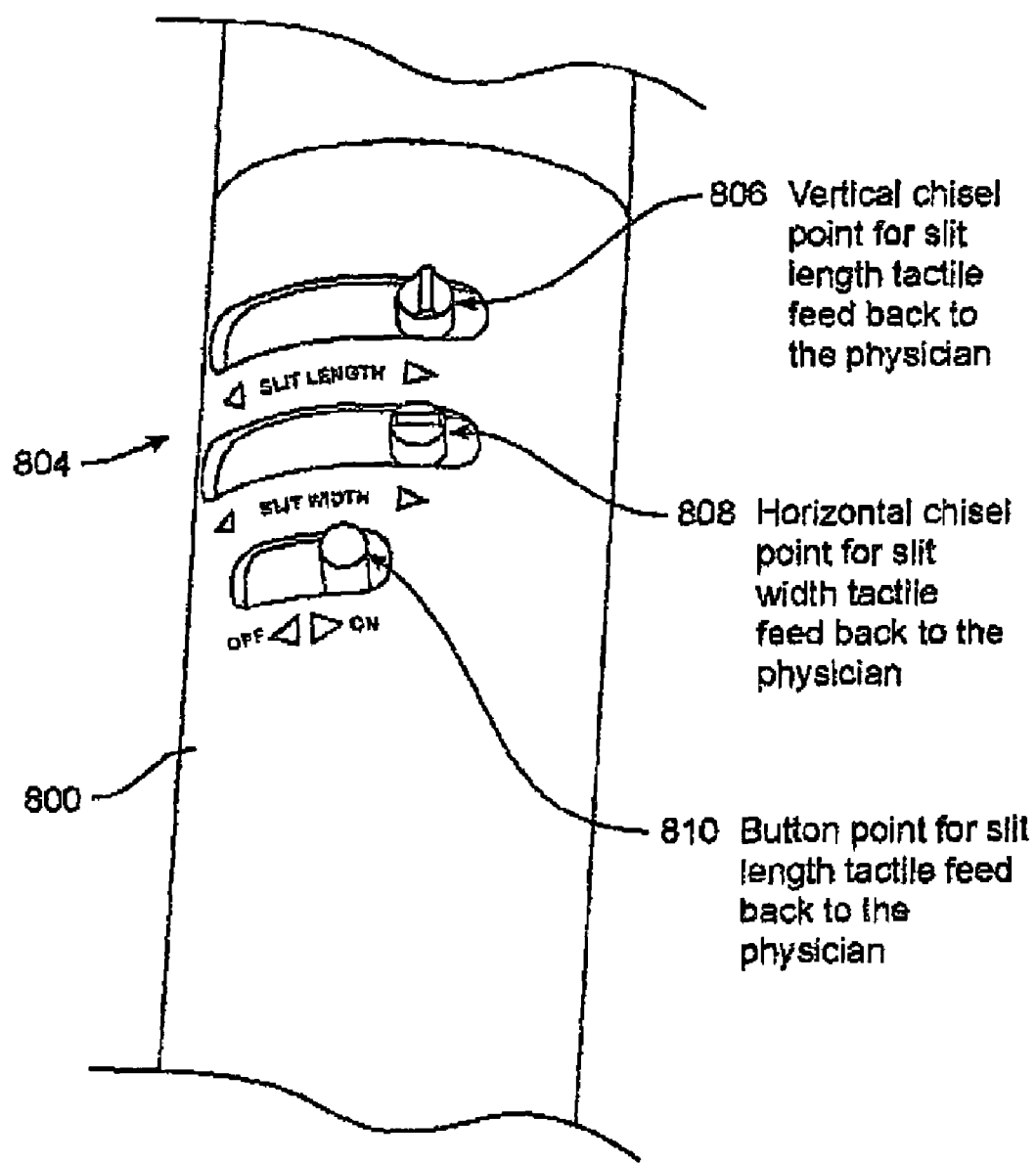
FIG. 8B illustrates controls having tactile feel in accordance with an embodiment of the present invention.

As illustrated in FIG. 8B, handle 800 comprises controls 804 having tactile features in accordance with an embodiment of the present invention. Each tactile feature corresponds to a control for adjusting the length, the width and the intensity of the projected beam of light. The slit length across the projected beam of light is adjusted with the sliding control as described above having a tactile feature comprising at least one vertical beveled edge such as a vertical edge of a vertical chisel point 806. The tactile feature comprising vertical beveled edges of vertical chisel point 806 provides tactile feedback to the operator as to the length of the slit. The operator is able to feel the feature through the sterile glove and the sterile handle cover as described above while the handle is supported by the hand of the operator. By feeling the feature comprising the vertical beveled edges of vertical chisel point 806 the operator determines that the control being adjusted controls the slit length. The operator adjusts the slit length control in response to the feeling.

The slit width across the projected beam of light is adjusted with the sliding control as described above having a tactile feature comprising at least one horizontal beveled edge such as a beveled edge of horizontal chisel point 808. The tactile feature comprising horizontal beveled edges of horizontal chisel point 808 provides tactile feed back to the operator as to the width of the slit. The operator is able to feel the tactile feature through the sterile glove and sterile handle cover while the handle is supported by the hand of the operator. By feeling the tactile feature comprising the horizontal beveled edges of horizontal chisel point 808 the operator determines that the control being adjusted controls the slit width. The operator adjusts the slit width control in response to the feeling.

An intensity of the projected beam of light is controlled with the sliding control as described above having a tactile feature comprising a rounded surface such as a button point 810. The tactile feature comprising the rounded surface of button point 810 provides tactile feed back to the operator as to the intensity of illumination. The operator is able to feel the feature comprising the rounded surface of button point 810 through the sterile glove and handle cover as described above while the handle is supported by the hand of the operator. By feeling the feature, the operator determines that the control being adjusted controls the intensity of illumination. The operator adjusts the intensity control in response to the feeling. In a preferred embodiment button point 810 turns the slit lamp beam on and off. In a preferred embodiment controls 804 have friction which improve control by the gloved operator.

Figure 9:
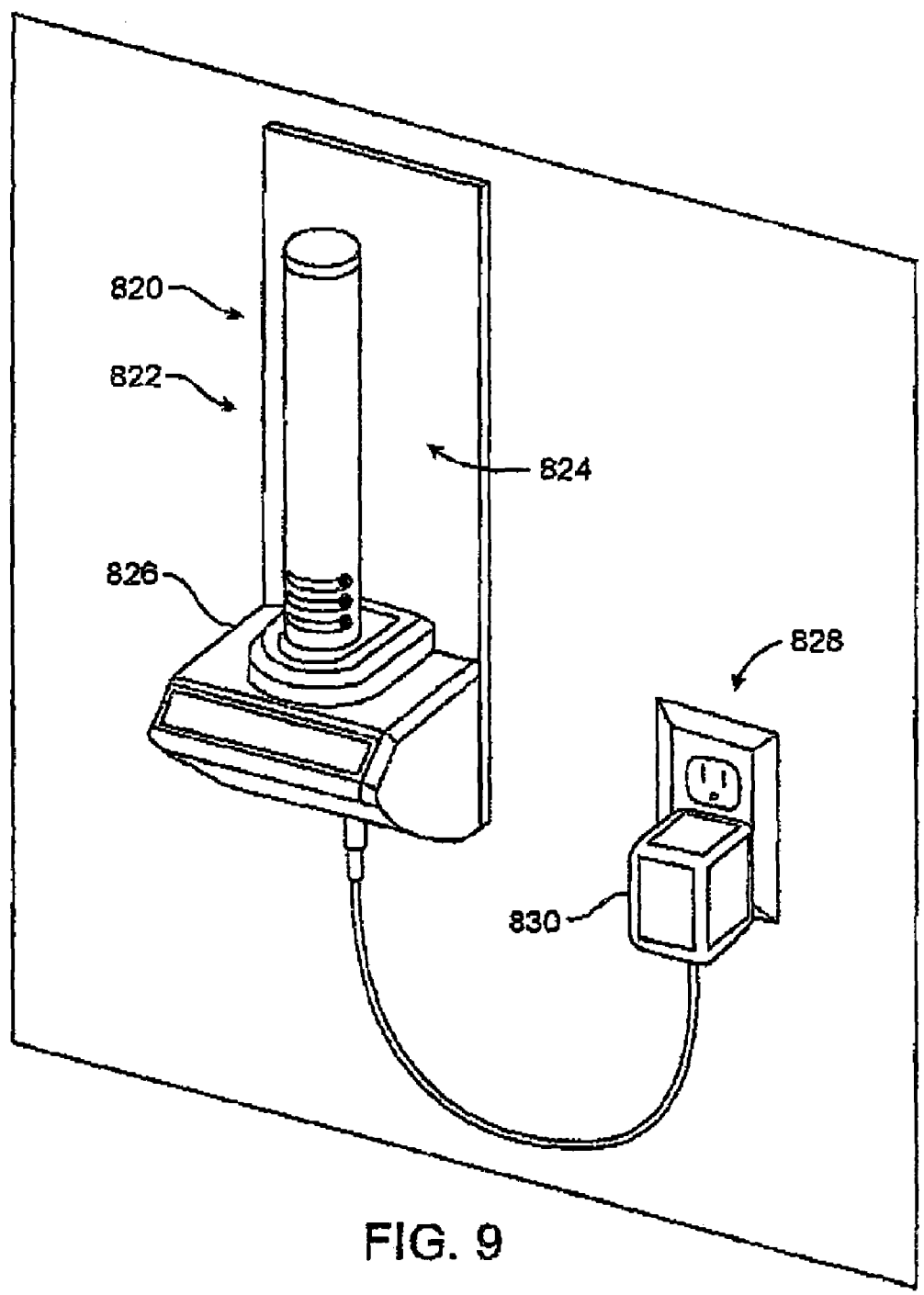
FIG. 9 illustrates a wall mounted slit lamp in accordance with an embodiment of the present invention.

As illustrated in FIG. 9, a wall mounted slit lamp 820 is mounted to a wall 822 in accordance with an embodiment of the present invention. Wall mounted slit lamp 820 comprises a base 826 and a backing plate 824 for receiving a sterile cover as described above. The sterile cover over backing plate 824 maintains sterility of the gloved operator as the operator grasps the handle of wall mounted slit lamp 820 while slit lamp 820 is covered by the sterile cover as described above and supported by base 826. In some embodiments slit lamp base 826 comprises a holder for a spare bulb (not shown). The wall mounted slit lamp can be mounted to any vertical surface including a wall of an operating room. The wall 822 preferably comprises a receptacle 828 for receiving a power supply 830 of the wall mounted slit lamp.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A slit lamp for illuminating an eye during ocular surgery, the slit lamp comprising:
   a light slit transmitting window;
   a handle manually supporting the window, the handle suitable for supporting the slit lamp with a hand of an operator;

a sterile cover covering the handle while the operator is holding the handle, at least a portion of the cover being flexible; and at least one adjustable control, the adjustable control being covered by the flexible portion and adjustable by operator manipulations with the hand through the flexible portion of the sterile cover.

2. The slit lamp of claim 1, further comprising a battery supported by the handle.

3. The slit lamp of claim 1 wherein the cover includes an opening disposed between the window and an end of the handle so that the window is exposed, while the cover is over the handle.

4. The slit lamp of claim 3 wherein the cover comprises an elongate body extending from the opening to an enclosed end.

5. The slit lamp of claim 1, further comprising:
a first control adjusting a width across a beam of light suitable for projection onto the eye;
wherein the first control is adjustable with operator manipulations through the flexible portion of the sterile cover.

6. The system of claim 5 further comprising a second adjustable control adjusting a length across the light beam illuminating the eye, wherein the second control is adjustable with operator manipulations through the flexible portion of the sterile cover.

7. The slit lamp of claim 6, wherein the first control and the second control are adjusted by sliding the controls with operator manipulations through the flexible portion of the cover.

8. The slit lamp of claim 6, wherein the first control and the second control are adjusted by rotating the controls with operator manipulations through a flexible portion of the cover.

9. The slit lamp of claim 6, wherein the first control and the second control are adjusted by applying pressure with operator manipulations through a flexible portion of the cover.

10. The slit lamp of claim 1, wherein the adjustable control adjusts an intensity of a light beam projected onto the eye.

11. The slit lamp of claim 1 further comprising a tactile feature configured to be felt by the operator through the cover while the handle is supported by the hand of the operator.

12. The slit lamp of claim 11 wherein the slit lamp has a plurality of controls, and wherein the feature corresponds to a control for adjusting at least one of a length, a width, and an intensity of the light beam such that the operator can identify the corresponding control with the hand.

13. The slit lamp of claim 11 wherein the feature comprises a tactile orientation feature located on the handle.

14. A slit lamp for illuminating an eye during ocular surgery, the slit lamp comprising:
a light slit transmitting window;
a handle manually supporting the window, the handle suitable for supporting the slit lamp with a hand of an operator;
a sterile cover covering the handle while the operator is holding the handle; and
a base charging a battery of the slit lamp, the battery supported by the handle;

wherein the cover comprises an opening, a portion of the slit lamp extending though the opening to the base while a battery of the slit lamp is charging, so as to permit the operator to remove the slit lamp from the base by grasping the handle covered with the sterile cover.

15. The slit lamp of claim 14, further comprising at least two electrical contacts passing electrical current between the base and the battery.

16. The slit lamp of claim 14, wherein the base comprises at least one coil of wire charging the battery with an inductive current.

17. The slit lamp of claim 14, wherein the slit lamp is used in conjunction with an operating microscope having a view of the eye while the slit lamp illuminates the eye.

18. The slit lamp of claim 14 wherein the charging base is attached to a laser refractive surgery system.

19. The slit lamp of claim 14 wherein the charging base is placed on a surface of a laser refractive surgery system.

20. A slit lamp system comprising:
a slit lamp comprising:
a handle having a proximal end and a distal end;
a window disposed distally of the handle, the window transmitting an elongate light beam suitable for illumination of the eye while the handle is supported by a hand of an operator; and
a battery supported by the handle, the battery coupled to a charge receiver disposed distally of the handle;
a slit lamp receptacle releasably supporting the slit lamp distally of the handle, the receptacle having a charge transmitter coupled to the charge receiver so as to charge the battery while the slit lamp is disposed therein; and
a sterile cover having an opening, a portion of the slit lamp extending through the opening to the receptacle while the sterile cover is disposed over the handle and a battery of the slit lamp is charging, so as to permit the operator to remove the slit lamp from the receptacle by grasping the handle covered with the sterile cover.

21. The slit lamp of claim 20 wherein the sterile cover is advanceable distally over the proximal end of the handle to facilitate sterile covering of the handle, and wherein the opening of the sterile cover is disposed proximally of the window when the sterile cover is positioned for sterile use.

22. The slit lamp of claim 20 wherein the receptacle is attached to a laser refractive surgery system having an operating microscope.

23. The slit lamp of claim 20 where in the receptacle is adapted to be positioned adjacent to a laser refractive surgery system having an operating microscope.

24. The slit lamp of claim 20 wherein the receptacle is attached to a laser refractive surgery system having an operating microscope.

25. The slit lamp of claim 20 further comprising a tactile feature which is felt by the operator while the handle is supported by the hand of the operator.

26. The slit lamp of claim 25 wherein the feature comprises a tactile orientation feature located on the handle.

27. The slit lamp of claim 25 wherein the feature corresponds to a control for adjusting any one of a length, a width, and an intensity of the light beam.

* * * * *